United States Patent [19]

McFadden

[11] Patent Number: 4,964,748
[45] Date of Patent: Oct. 23, 1990

[54] POSITIONING DEVICE

[76] Inventor: Joseph T. McFadden, 513 Mowbray Arch, Norfolk, Va. 23507

[21] Appl. No.: 360,306

[22] Filed: Jun. 2, 1989

[51] Int. Cl.⁵ ............................................... F16B 7/10
[52] U.S. Cl. ........................................ 403/55; 403/84; 248/276
[58] Field of Search ...................... 403/55, 54, 56, 84; 248/276, 160

[56] References Cited

U.S. PATENT DOCUMENTS

| | | | |
|---|---|---|---|
| 3,278,207 | 10/1966 | Barish et al. | 403/55 |
| 4,157,876 | 6/1979 | DiGiulio | 403/90 |
| 4,402,481 | 9/1983 | Sasaki | 403/55 X |
| 4,431,329 | 2/1984 | Baitella | 403/55 |
| 4,585,195 | 4/1986 | McFadden | 403/374 X |

Primary Examiner—Andrew V. Kundrat
Attorney, Agent, or Firm—Cushman, Darby & Cushman

[57] ABSTRACT

A device for precisely positioning and locking an object in a selected position includes a first arm member having one end for engaging a base support and for clamping the base support and an opposite end on which is rotatably mounted a bracket in a clamping device at the second end; the first arm member includes a single locking lever for actuating simultaneously both of the clamping devices; the bracket member is pivotably connected to a second arm member which has clamping devices at its opposite ends and a single locking lever for actuating and releasing the clamping devices. One end of the second arm member is pivotably mounted on the bracket member for rotation about a selected axis while the opposite end is connected to another bracket member for rotation about an axis that extends transverse to the axis of rotation of the first bracket member; the second bracket member is connected to a third arm member which includes a single clamping device for a ball rotatably carried in a ocket to which a mounting pin is attached.

7 Claims, 2 Drawing Sheets

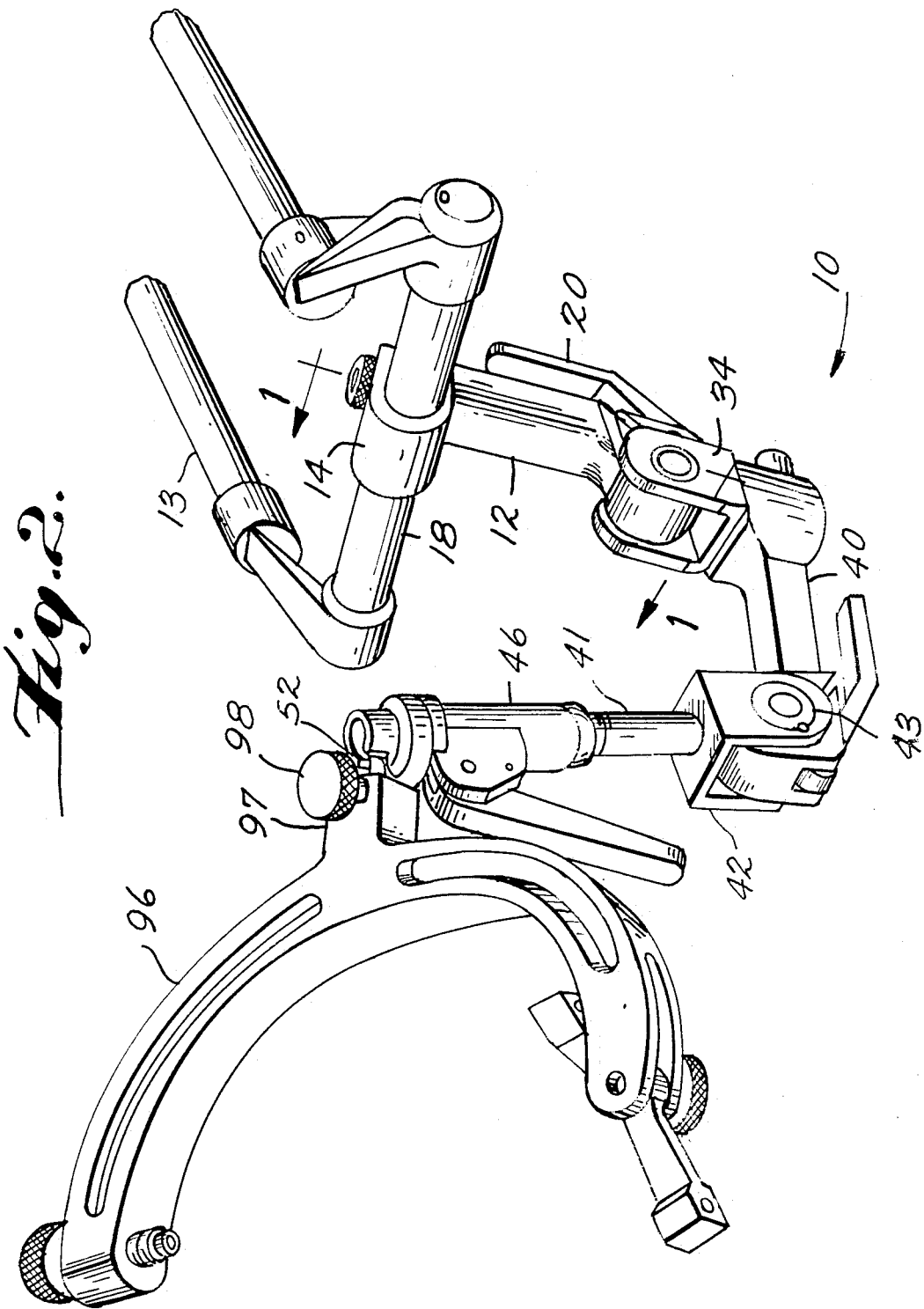

POSITIONING DEVICE

FIELD OF THE INVENTION

The present invention relates to a positioning device for an object, and, more specifically, to a device that will permit a user to position the object with one hand and to lock the positioning device in the desired orientation with his other hand, thus greatly facilitating the precise positioning of the object. The positioning device has particular utility in certain surgical procedures where repositioning of a surgical site, such as the head of a patient, is required during a procedure.

BACKGROUND OF THE INVENTION

Generally, support devices for a portion of the anatomy of a patient that have been employed in medical procedures have emphasized stability and rigidity in their structures at the expense of ease of adjustment in view of the recognized importance in guarding against undesired movement of the patient during the medical procedure being carried out. For example, in U.S. Pat. No. 4,157,876, a lockable, universally articulated joint in an orthopaedic appliance is disclosed. A locking member is also provided which includes a locking screw which extends through a socket and is threaded into a locking device. When the locking screw is loosened, the locking member allows universal articulation between the movable elements while preventing separation of these elements. Tightening of the screw effects clamping of the movable elements. Such a device as well as others of a similar nature do not provide the precise positioning and any facility in repositioning of the surgical site such as the head of a patient when used in conjunction with a headrest required in neurological surgery. See in this regard, U.S. Pat. No. 4,585,195 and Canadian Patent No. 823556. While these and similar devices have enabled the user to securely lock in a desired position the object upon which a procedure is to be carried out, they also generally suffer from the disadvantage of consuming a considerable amount of time to effect the original positioning and render impractical repositioning of the object during the operating procedure. This is a particularly serious disadvantage in neurological surgery, as such procedures generally consume a lengthy amount of time, so that where repositioning cannot be readily accomplished, the surgeon is required to operate in awkward positions which can greatly contribute to fatigue and result in lengthening of the time required to carry out the procedure. Where a device incorporates a plurality of universal joints, each of which must be separately and manually locked and unlocked to effect repositioning, there is always the possibility of overlooking one of the locking devices in carrying out any repositioning that is effected thus increasing the potential for injury to the patient.

SUMMARY OF THE INVENTION

The present invention provides a positioning device which will allow a user to precisely position an object in a desired position with one hand and to lock the positioning device with the other hand in a safe and secure manner and yet will enable the user to effect repositioning of the object much more rapidly and safely than has heretofore been possible with the prior art positioning devices.

In a preferred embodiment, the present invention comprises three arm members and associated locking devices. The first two of the arm members each have opposite ends having locking members which are actuated by a single lever. The first one of the arm members has one end adapted to be attached to a support such as a workstand or table, so as to be pivotable through substantially 360° about the support. At its opposite end, the first arm member is provided with a bracket rotatably mounted thereon, with this end of the first arm member having a locking device for locking the bracket in a desired position upon actuation of the locking lever of the first arm. The second arm receives a pin projecting from the bracket of the first arm at one end of the second arm, and at its opposite end, a second bracket is pivotably mounted. The second arm is rotatable about the pin of the first bracket through 360° while the second bracket is pivotable about the second end of the second arm through an angular degree limited only by its engagement with the second arm. The second arm has a locking lever for locking each of its opposite ends with respect to the pin of the first bracket and a shaft on which the second bracket is mounted.

Extending from the second bracket is a third arm member having its first end securely connected to the second bracket. At its opposite end, the third arm member is provided with a ball and socket device with a pin member extending from the ball and to which can be secured a suitable device such as a clamp, headrest, or the like. The third arm member has a locking device operated by a locking lever for locking the positioning pin in a desired position.

The locking levers are preferably of the type that are pivotably mounted at one end of each associated arm member and are each connected to a rod that extends through a bore formed in the associated arm member. The locking device at each end of the first and second arms comprises a clamping element which is generally U-shaped, having at least one free leg which will be pulled towards an oppositely located surface of the arm member about an axis of rotation which will include a shaft on which an associated arm member or bracket member is mounted. Actuation of a locking lever from an unlocked to locking position will effect movement of an associated rod to move the free leg of an associated clamping end from an unlocked to a locked position. Due to its structure, the free leg will have a natural resiliency urging it to move to its open position so that when a locking lever is released, the free leg will move from its locked position to a released condition.

By providing a double locking action at each end of each of the first and second arm members which is operable by a single locking lever, much greater facility will be afforded the user than in a device where completely separate locking elements must be provided for each end of the first and second arms.

The present invention, therefore, provides a locking device which is simple in construction and will afford ready connections to other locking devices to permit adaptability to a wide variety of uses.

The foregoing and other advantages will become apparent as consideration is given to the following detailed description taken in conjunction with the accompanying drawings, in which:

BRIEF DESCRIPTION OF THE DRAWINGS

FIG. 2 is a perspective view showing the positioning device of the present invention mounted on a support shaft and bracket together with a headrest of the type used in neurological surgery.

DETAILED DESCRIPTION OF THE INVENTION

Figure 1:
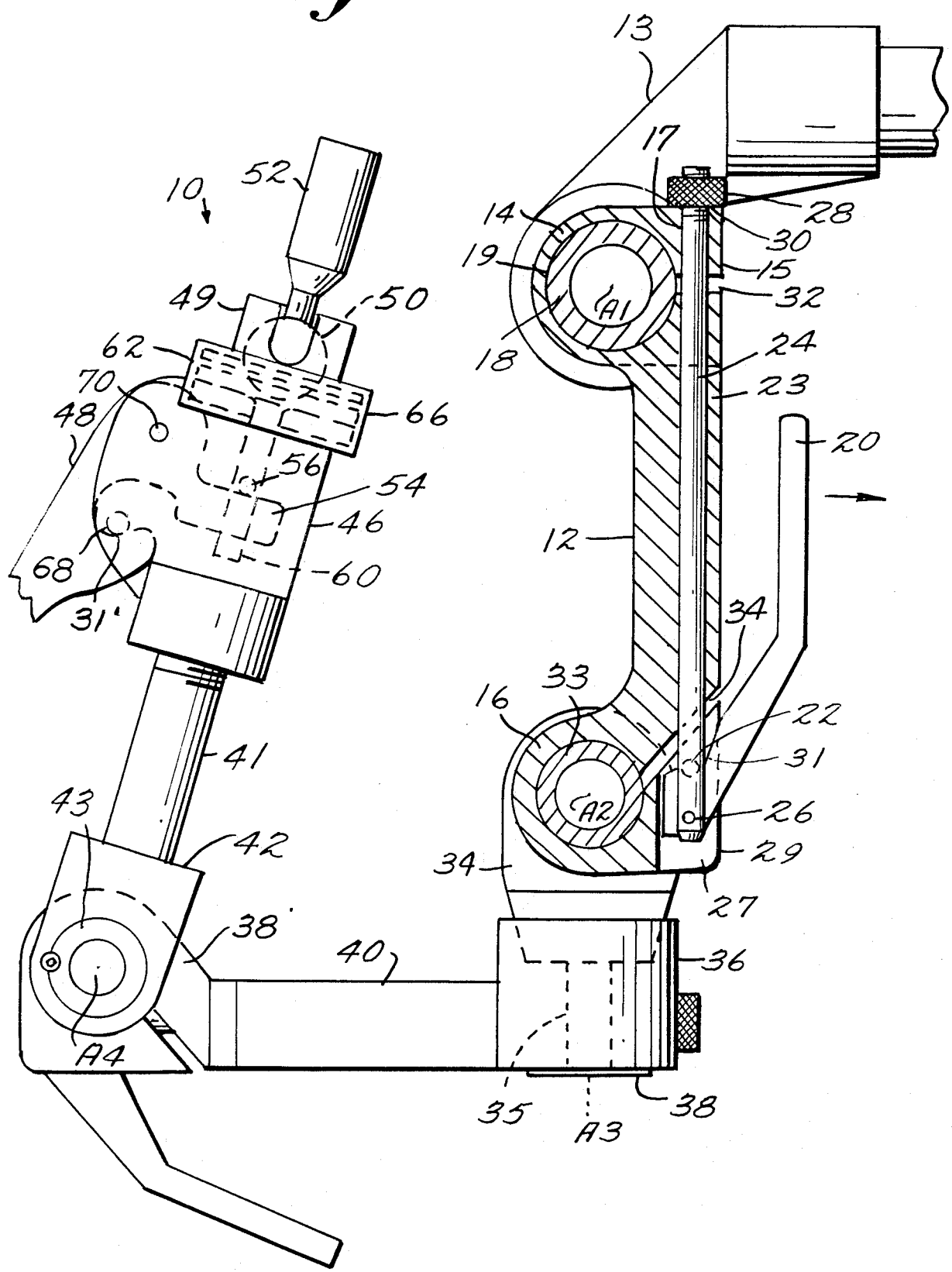
FIG. 1 is a side view in elevation, partly in section of the positioning device of the present invention.

Referring now to the drawings wherein like numerals designate corresponding parts throughout the several views, there is shown the device 10 of the present invention mounted on a table bracket 13, more fully illustrated in FIG. 2. The bracket 13 includes a shaft 18. The device 10 includes a first arm member 12, a second arm member 40, and a third arm member 41. The first arm member has at one end a clamping device 14 mounted on the shaft 18 of the bracket 13. The clamping device is generally U-shaped and has a free leg 15 having a generally cylindrical recess 19 for closely interfitting engagement with the external shaft surface of the shaft 18. Leg 15 is provided with a bore 17 for receiving a rod 24 which also extends through a bore 23 formed through the body of the first arm member 12. The rod extends to a second clamping member 16 located at the opposite end of the first arm member 12. The bore 23 is extended through the leg 15 so that the rod 23 may extend through the leg 15 as illustrated. The exposed end of the rod 23 is threaded to receive a threaded retaining ring 28. The opposite end of the rod 24 is provided with a bore for receiving a retaining pin 26 which connects the end of the rod 24 to a locking lever 30 as illustrated. On the inner side of its end adjacent to pin 26, locking lever 20 is provided with a camming surface 31. Recess 27 is provided on one wall thereof with a lug 22 which is positioned to engage the camming surface 31 of locking lever 20. The camming surface 31 is shaped so that as the lever 20 is rotated clockwise as viewed in FIG. 1, rod 23 will move to allow legs 15 and 29 to move away from the main body portion of the first arm member 12 to thereby open or release the clamping devices 14 and 16 substantially simultaneously. Rotation of the locking lever 20 in the counter-clockwise direction as viewed in FIG. 1 will result in movement being transmitted to free legs 29 and 15 towards one another until the over-center position is reached on the camming surface 31 which, upon engagement with the lug 22 will effect locking of the lever 20 in the leftward-most position and secure clamping of each of the clamping devices 14 and 16 about the associated elements 18 and 20

The degree of clamping force exerted can be varied by loosening or tightening the threaded ring 28 on the threaded end of the rod 24.

The gaps 32 and 34 in the clamping devices 14 and 16, respectively, are dimensioned to provide the required amount of play in the free legs 15 and 27, respectively.

A first bracket member 34 includes a shaft 33 which is rotatably received within the clamping device 16 of the first arm member 12 so as to be rotatable about axis A2. Axis A2 extends parallel to axis A1 of clamping device 14. The first bracket member 34 includes a pin shown in phantom lines at 35.

The second arm member 40 is identical to the first arm member 12 with the exception that the clamping devices 36 and 38 have their respective axes, A4 and A3, extending perpendicular to each other. The clamping device 36 surrounds pin 35 of first bracket 34. The free end of the pin 35 is provided with a retaining plate 38 so that when clamping device 36 is in its released condition, the first arm member 40 will remain connected to the first bracket 34 for free rotation about pin 35. The remaining elements of the second arm member 40 will not be described as they are identical in form and operation to the corresponding members of first arm member 12.

A second bracket member 42 includes a shaft 43 received in clamping device 38 whereby the bracket 42 is pivotable about an axis A4 which extends, as noted above, perpendicular to axis A3 of clamping device 36.

Bracket 42 includes a third arm member 41 which, at its distal end, is connected to a fifth locking device 46 and its associated locking lever 48. The free end of the locking device 46 supports a socket housing 49 in which is located a ball member 50 to which is securely attached as by welding or by threaded interconnection, a pin 52. As illustrated, in phantom lines, actuation of the lever 48 in a counter-clockwise direction, as viewed in FIG. 1, will move arm member 54 upwardly to engage a pin 56 which is carried by a shaft 60. The upper end of the shaft 60 is connected to a movable plate 62 which has a recess shaped to closely conform to that of the ball 50. Thus, movement of the plate 62 toward the housing 49 will effect locking of the ball 50 in a desired position. Housing 49 may be provided with a slot or recess 64 for permitting greater angular freedom of movement of the pin 52 relative to the housing 49. Further, housing 49 and its associated ball and pin 52 may be rotatable about the longitudinal axis of the arm member 41 in a housing 66 located on the end of the clamping device 46. Locking lever 48 will be provided with a camming surface 31' similar to that employed with the locking levers for arm members 12 and 40 and will cooperate with a pin 68 for maintaining the locking lever 48 in its locked position. The lever 48 is pivotably mounted on a pin 70 carried by an extension of the housing for the locking device 46.

With reference now to FIG. 2, there is shown the device 10 of the present invention with a neurological headrest 96 secured to the pin 52. For this purpose, the base 97 of the headrest is provided with a cylindrical bore of a size for closely interfitting reception of the pin 52. A transverse threaded bore is provided in the base 97 for receiving a tightening screw 98.

In use, the surgeon may secure the headrest 96 to the head of a patient while the locking levers of the device 10 are all in their unlocked position. Then, upon selecting the desired position for the head of the user, the surgeon, with his free hand, may simply lock the associated levers of each of the arm members 12, 40, and 41 to thereby securely stabilize the position of the head of the patient as desired. During a surgical procedure, when it is desired to adjust the position of the head of the patient, for example, by a slight rotation thereof, the surgeon need merely release locking lever 48 while holding the patient's head. After tilting the patient's head, the surgeon simply relocks lever 48 to hold the patient's head in the new tilted position. It will be apparent that by releasing all of the locking levers, complete freedom of movement of the patient's head in three dimensions can be effected with great accuracy and speed.

Having described the invention, it will be apparent to those skilled in the art that various modifications may be made thereto without departing from the spirit and scope of this invention as defined in the appended claims.

What is claimed is:

1. A device for positioning of an object relative to a base comprising:

first, second and third arm means, said first and second arm means each having first and second opposite ends, each said end of a said respective first and second arm means having clamp means movable between a locked and unlocked position, said first and second arm means each further including movable actuating means for substantially simultaneously moving each said clamp means of said respective first and second arm means between said locked and unlocked positions in response to movement of said respective actuating means between an actuated and a deactuated position, a first bracket means including shaft means releasably and rotatably engaged by said clamp means of said second end of said first arm means, said first bracket means further including pin means releasably engaged and retained by said clamp means of said first end of said second arm means so that said second arm means is rotatable about said pin means when said respective clamp means of said second arm means is in an unlocked position, a second bracket means including another shaft means releasably and rotatably engaged by said clamp means of said second end of said second arm means, said third arm means having a first end rigidly mounted on said second bracket means so that said third arm means is movable therewith, said third arm means having a second end opposite said first end thereof provided with a movable mounting member and locking means for locking said mounting member in a selected position relative to said third arm means.

2. The invention as claimed in claim 1, wherein said clamp means of said first and second arm means comprises a collar portion defining a shaft receiving area and a leg member having a free end spaced from said respective arm means and movable toward said respective arm means to reduce the size of said area when said respective clamp means is moved to the locked position.

3. The invention as claimed in claim 2, wherein, for each said first and second arm means, said respective free ends of said respective clamp means are connected by rod means to said actuating means.

4. The invention as claimed in claim 3, wherein each said first and second arm means includes a body portion and a bore in said body portion extending between said clamp means in which said rod means is disposed.

5. The invention as claimed in claim 4, wherein said rod means has first and second ends and said first end extends through a bore formed in said free end of said respective leg member at said first end of said respective first and second arm means and terminates in a threaded portion which carries a threaded retaining member thereon for allowing adjustment of the position of said rod means, said second end of said rod means being connected to said free end of said leg member at said second end of said respective arm means by a pin.

6. The invention as claimed in claim 5, wherein said actuating means comprises a lever having a cam surface and said second end includes a lug engaged by said cam surface, said lever being pivotally mounted on said respective second end of said respective arm means.

7. The invention as claimed in claim 6, wherein said lever is pivotally mounted on said pin to which said lever is mounted.

* * * * *